United States Patent [19]

Shillington

[11] Patent Number: 5,249,680
[45] Date of Patent: Oct. 5, 1993

[54] ROTARY CONTAINER TOP WITH NEEDLE REMOVER SLOT

[75] Inventor: Richard A. Shillington, Leucadia, Calif.

[73] Assignee: Med-Safe Systems, Inc., Carlsbad, Calif.

[21] Appl. No.: 946,938

[22] Filed: Sep. 17, 1992

[51] Int. Cl.$^5$ .................. B65D 83/10; B65D 51/24
[52] U.S. Cl. .................................................. 206/366
[58] Field of Search ................................ 206/365, 366

[56] References Cited

U.S. PATENT DOCUMENTS

| | | | |
|---|---|---|---|
| 4,502,606 | 3/1985 | Shillington | 215/274 |
| 4,667,821 | 5/1987 | Shillington | 206/366 |
| 4,984,686 | 1/1991 | Shillington | 206/366 |
| 5,085,338 | 2/1992 | Inagaki | 206/366 X |
| 5,127,522 | 7/1992 | Ranford | 206/366 |

Primary Examiner—William I. Price
Attorney, Agent, or Firm—Baker, Maxham, Jester & Meador

[57] ABSTRACT

A needle removal closure for a disposable container having a circular opening defined by a circular rim comprises a circular closure rotatably mounted on the rim within the circular opening, a ratchet device constraining the closure to rotate in a single direction, and a needle removal slot in the circular closure offset from the rotary axis thereof and oriented in a direction for gripping a needle hub inserted therein and moved in the direction of rotation of the circular closure for unthreading of a needle.

20 Claims, 3 Drawing Sheets

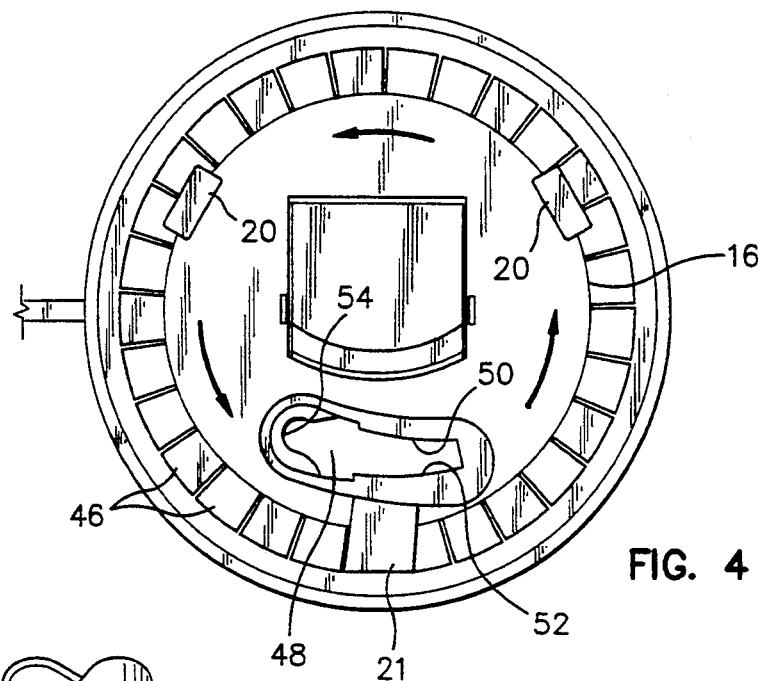
FIG. 4
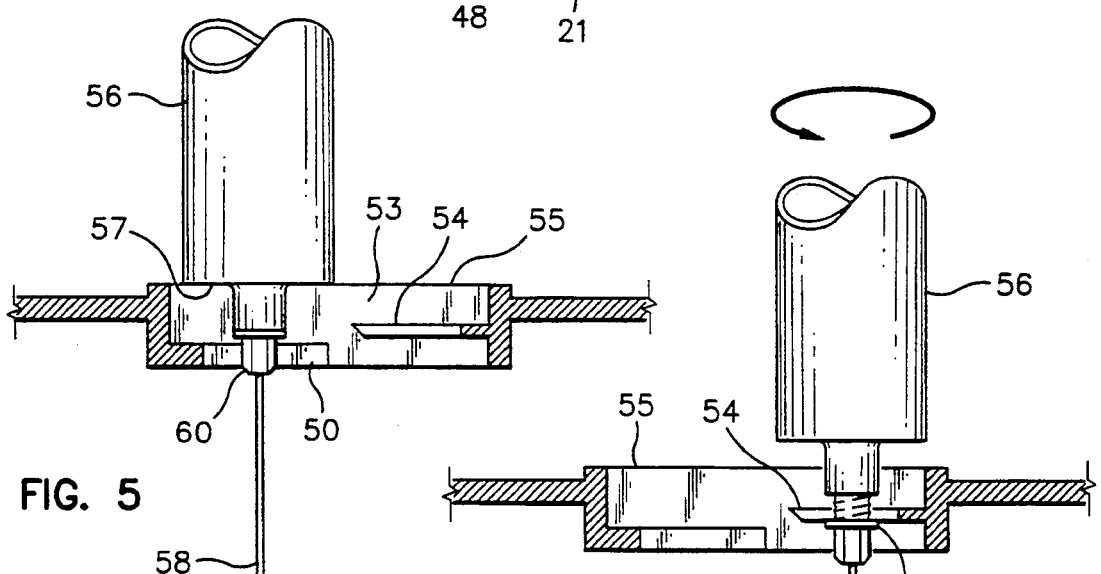
FIG. 5
FIG. 6
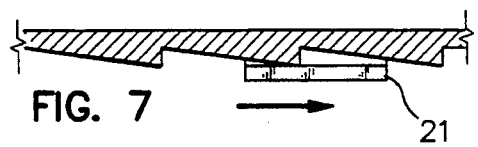
FIG. 7
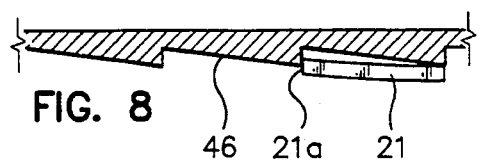
FIG. 8

ROTARY CONTAINER TOP WITH NEEDLE REMOVER SLOT

BACKGROUND OF THE INVENTION

The present invention relates to disposable sharps containers and pertains particularly to an improved rotary top and needle remover slot for disposable sharps containers.

Disposable containers have been developed in recent years which provide a reasonably high degree of security for disposable articles, such as needles and surgical blades known as sharps, and other similar articles and materials, to keep them out of the hands of unauthorized persons and to keep them from being reused. These containers are designed with restricted access openings and closures to prevent the removal of materials from the container under ordinary circumstances.

One such container of the aforementioned type is that of our prior U.S. Pat. No. 4,502,606, issued Mar. 5, 1985, and directed to a locking closure for disposable containers. These containers are also provided with needle removal tools in the form of one or more slots which act as a wrench for removal of the needles from syringes and the like. These needle removal tools are not only convenient, but also provide a safe means for removal of the needle. The safe removal of the needle is essential to protect hospital personnel from certain highly contagious diseases.

Many prior disposable containers have had needle removal tools built into the top thereof adjacent the disposal opening. This is a convenient and desirable arrangement. However, these are in need of improvement.

In my prior U.S. Pat. No. 4,667,821 entitled "SWIVEL TOP CLOSURE FOR PHLEBOTOMY CONTAINER", I disclose a rotary container top with a slot for quick removal of a syringe needle. The needle engaging slot in that patent is positioned offset from the rotary axis of the top so that when the needle is engaged by the slot and the top rotated, the needle is unscrewed from the syringe body. The syringe body is then moved in the reverse direction to disengage the needle from the wrench portion of the slot, and engages a hooking portion to disengage the needle from the syringe barrel. However, the container top sometimes rotates in the opposite direction and frustrates attempts to dislodge the needle from the slot and/or the barrel.

Improvements have been made in needle removal slots, such as covered in my U.S. Pat. No. 4,984,686, issued in Jan. 15, 1991, for more securely fitting variations in needle hub sizes. These new slots are tapered so that the needle hub is wedged therein and gripped more tightly than in most prior art slots. Thus, the top is even more likely to rotate in the opposite direction and make the needle more difficult to dislodge without holding the container top.

It is, therefore, desirable that a disposable container with improved rotatable closure and needle removal slots be available.

SUMMARY AND OBJECTS OF THE INVENTION

It is the primary object of the present invention to provide an improved sharps container having an improved closure and needle removal slot.

In accordance with a primary aspect of the present invention, a needle removal device comprises a rotatable closure having a needle engaging slot offset from the rotary axis for engagement with the needle hub for unthreading the needle as the closure is rotated in one direction, with means for preventing rotation in the opposite direction.

In accordance with another aspect, the needle slot is a converging slot with spacer means for precisely positioning the needle hub within the slot, and with flange hook for engaging the needle flange for applying an axial force.

BRIEF DESCRIPTION OF THE DRAWING

The above and other objects and advantages of the present invention will become apparent from the following description when read in conjunction with the accompanying drawings wherein:

FIG. 4 is a plan view of the bottom of the top looking up from inside the container, section view taken on line 4—4 of FIG. 2;

FIG. 5 is a section view taken on line 5—5 of FIG. 2 showing a syringe added in a first position;

FIG. 6 is a view like FIG. 5 showing a second position of the syringe assembly;

FIG. 7 is a detailed section view taken showing a first position of an anti-rotation device; and FIG. 8 is a view like FIG. 7 showing a second position of the device.

DETAILED DESCRIPTION OF A PREFERRED EMBODIMENT

Figure 1:
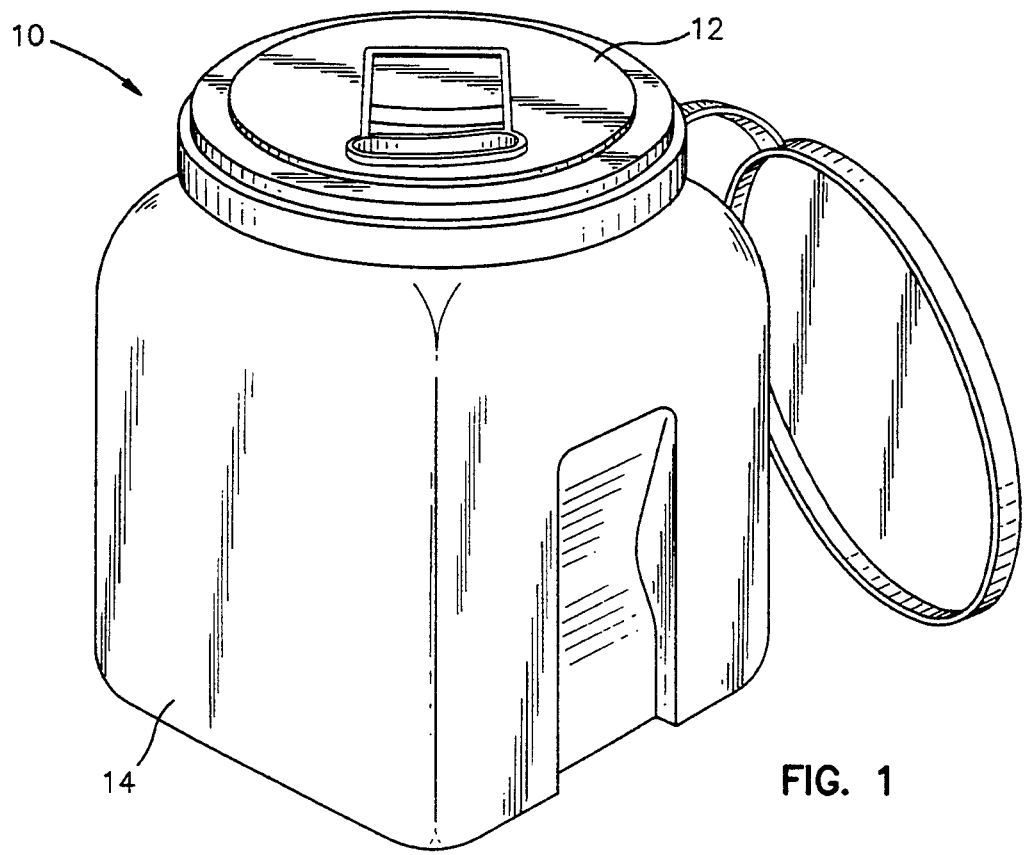
FIG. 1 is a perspective view illustrating a preferred embodiment of the invention.

Referring to FIG. 1 of the drawing, a closure in accordance with the invention is shown installed in the opening of a disposable container, the entire assembly being designated generally by the numeral 10. The closure 12 comprises a flat circular disc that is designed to rotatably mount in a circular opening in a container. The closure is shown rotatably mounted in an opening of a container 14. The container may be disposable or reusable as will be further described.

The closure 12, as previously stated, comprises a flat circular disc defined by a circular peripheral edge 16, and having an upper overlapping radially extending flange 18 extending outward beyond the peripheral edge 16. The flange 18 is preferably formed on the top side of the closure for overlapping and engaging the upper surface of the wall area around and forming a circular opening in a container. A plurality of tabs 20 extend outward from the inside surface of the closure disc, overlapping and extending outward beyond the peripheral edge 16 for overlapping the inside surface of a wall surrounding a circular opening in a container. The construction of the closure is such that it is free to rotate with slight resistance within the opening within which it is mounted. The closure 12 is constructed to rotate in one direction only about the central axis thereof.

Figure 3:
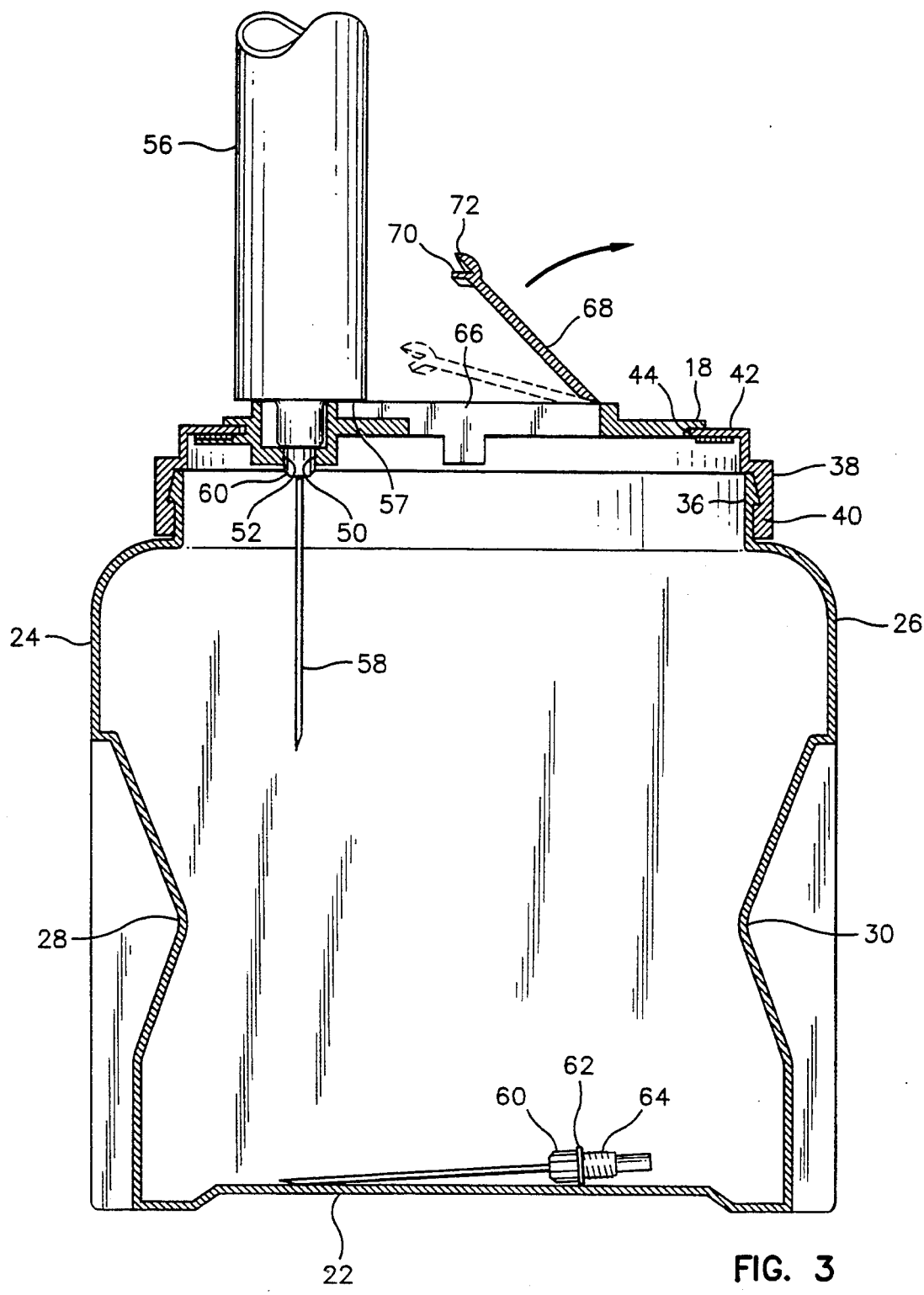
FIG. 3 is a front elevation view in section taken on line 3—3 of FIG. 2 with a syringe shown in position to show the cooperative relationship.

The closure is constructed to be mounted in any container. However, the closure is illustrated in conjunction with, and is particularly suitable for disposal of phlebotomy syringes. The container 14 is of a generally square box-like configuration having a generally flat square bottom 22, with a first pair of opposite side walls 24 and 26 extending upward therefrom, and having recesses 28 and 30 therein for the purpose of mounting in a suitable bracket. The opposite sides 32 and 34 are generally flat square panels. The top of the container converges to a circular top, with the arrangement shown with a circular neck or lip 36 for receiving a circular closure rim 38. The closure rim 38 has a mounting flange 40 for engaging and locking to lip 36, and having an inwardly directed wall 42 in which is formed a circular opening 44 within which the closure 12 is mounted. As best seen in FIGS. 3 and 4, the flange 18 overlaps the wall 42 on the top side, and the tabs 20 and 21 overlap the wall 42 on the inside, thus retaining the closure 12 in position in the opening of the container for rotation therein.

The rotating disc closure member 12 is constructed in conjunction with the circular mounting rim 38 to rotate in one direction (needle unthreading) only. This is accomplished by means of a ratchet and pawl like mechanism as illustrated in FIGS. 4, 7 and 8. A series of ramp like ratchet teeth are formed around the opening 44 on the inside of closure rim 38. The tab 21 is constructed to act as a pawl and ride over the ratchet teeth 46 in one direction (FIG. 7). However, in the opposite direction, an edge 21a engages an edge of the teeth 46 and restrains or prevents rotation of the disc 12 in the opposite direction.

A needle wrench in the form of a closed end tapered slot or aperture 48 is formed in the closure member 12, spaced from the central or rotary axis thereof for defining a crank arm as will be explained. The needle wrench comprises a slot having a wide end portion and converging side walls 50 and 52. The converging sides define a variable span wrench for engaging and coupling the flute portion of a hub of a needle. The enlarged portion of the slot is sufficiently wide to define an opening to enable a standard needle with its flange to fall therethrough. The slot is mounted within a cavity formed by side walls 53 that terminate in an upper spacer surface or edge 55. The spacer surface is positioned above the slot so that when an end 57 of a barrel engages it, the flutes 60 of the needle will be precisely positioned to engage the slot walls 50 and 52. The user will not have to hunt and feel for the slot.

The wrench end of the slot is designed to engage the hub of the needle for applying a rotatable torque thereto for unscrewing the needle from the barrel. The needle engaging portion of the slot can have any suitable configuration for coupling to a needle hub. However, the converging slot as disclosed herein is preferred. The slot as disclosed and described herein is an improvement over the slot disclosed in commonly assigned U.S. Pat. No. 4,984,686, issued Jan. 15, 1992. An extraction lip or rim 54 in the opposite end of the wrench assembly is formed by a C-shaped portion of the disc that is less in thickness than the disc. This C-shaped rim is designed to serve as a hook or puller for hooking the flange underneath thereof, as shown in FIG. 6, for applying axial force to the needle, if needed, for pulling it from the threaded bore of a barrel. The C-shaped rim 54 is positioned above the top of slot 50, 52 an amount slightly greater than the thickness of the needle flange, so that the flange slips beneath it when moved to that end of the slot. The rim 54 is positioned relative to positioning surface 55, so that the needle rim is positioned beneath it.

Referring to FIGS. 3, 5 and 6, there is illustrated a syringe barrel 56 having a needle 58 mounted therein. The needle, as can be best seen in FIGS. 3, 5 and 6, includes a fluted hub 60 with a disc-like radial flange 62 separating the hub from a threaded portion 64. The threaded portion 64 is designed to engage and fit internal threads in a bore on the end of the barrel 56 for holding or securing the needle in place. The hub 60 is engaged by tools, such as a wrench slot, for removing the needle from the barrel.

Figure 2:
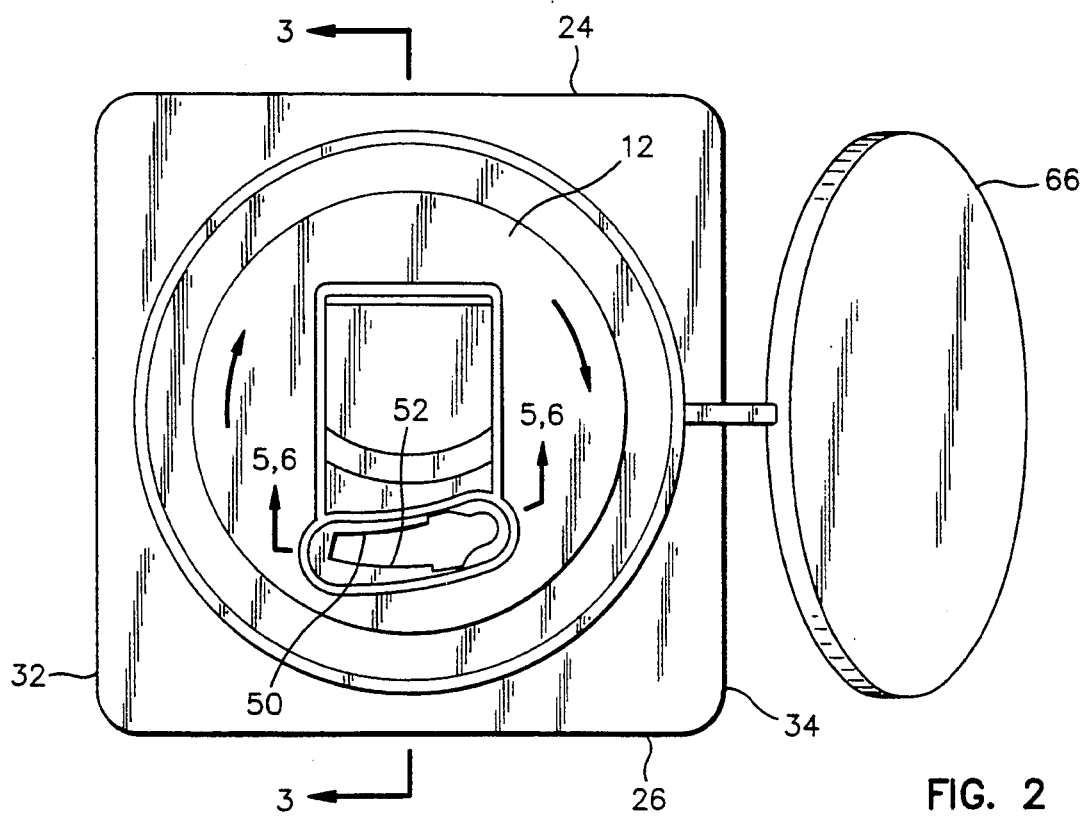
FIG. 2 is a top plan view of the embodiment of FIG. 1.

When it is desired to remove the needle, the barrel is grasped in the hand and the needle extending into the wrench slot, so that an end 57 of the barrel engages spacer rim 55 and positions flutes 60 of the hub so that the wrench portion of the slot (side walls 50 and 52) engages the hub 60, as shown in FIGS. 3 and 5. Rotation of the closure in a clockwise direction, as shown in FIG. 2, utilizing the barrel 56 as a crank handle applies a counterclockwise rotation to the needle relative to the barrel. As shown in FIG. 5, continued rotation of the closure around its axis results in the needle becoming unscrewed from the barrel, as shown in FIG. 6.

When the needle is completely unscrewed, the barrel is slipped toward the wide portion of the slot, such that the flange 62 of the needle passes beneath rim 54 can pass down through the slot into the barrel or container. Should for some reason the needle be still frictionally held to the barrel, the threaded portion of the needle is slipped into the slot portion 54 such that the flange 62 is below the rim surface, as shown in FIG. 6. The barrel 56 is then lifted for gripping or hooking the flange 62 of the needle so that the barrel can be pulled from the needle, letting the needle fall into the bottom of the container.

An additional opening 66, which may be a somewhat square opening, as shown in FIG. 3, may be formed in the closure disc 12 for receiving other disposable items, such as barrels and the like. A pivoting closure tab 68 is pivotally mounted by a hinge in the closure for pivoting to selected positions over the opening 66, as shown in FIGS. 2 and 3, for closing the opening or movable to positions to either side of the opening to provide access thereto. A pair of detent member 70 may be formed by the edge of the closure 68 for holding the closure in closed position. Flutes or ridges 72 may be formed on the top of the closure 68 for enabling ease of gripping and application of a force thereto for pivoting the closure to its open position.

The closure is designed to be flat, as illustrated, such that it can be used in conjunction with locking closures, such as disclosed in U.S. Pat. No. 4,502,606, granted Mar. 5, 1985, of which I am a co-inventor. These closures include a second cap or permanent closure 66, which when the container is full and ready to be disposed of, can be locked in place over the closure such that access to the interior of the container is prevented.

The illustrated container is designed to be mounted in a holder for holding it in position, such that the above described operation of removing a needle can be carried out by one hand. To this end, a mounting bracket is illustrated in FIG. 4 of my prior U.S. Pat. No. 4,667,821, which comprises a base member designed to be attached to a table top or other suitable support surface. A pair of spring clip fingers extend upward and include inwardly directed gripping tips for extending into the recesses 28 and 30 of the container. Thus, the holder is designed to grip the container and hold it against rotation to permit rotation of the closure without having to hold the container.

While I have illustrated and described my invention by means of specific embodiments, it is to be understood that numerous changes and modifications may be made therein without departing from the spirit and scope of the invention as defined in the appended claims.

I claim:

1. A needle removal closure assembly for a disposable container comprising:
   a disposable container having a circular opening defined by a circular rim;
   a circular closure rotatably mounted on said circular rim within said circular opening;
   means constraining said closure to rotate in a single direction of rotation; and
   needle removal slot means in said circular closure offset from the rotary axis thereof and oriented in a direction for gripping a needle hub inserted therein and moved in said direction of rotation of said circular closure for unthreading of a needle.

2. A closure assembly according to claim 1 wherein said needle removal slot means comprises an elongated converging slot defined by opposed walls converging in said direction of rotation.

3. A closure assembly according to claim 1 wherein said needle removal slot means is mounted in a recess in said closure, said recess formed by upstanding walls defining positioning means for engaging a barrel of a syringe for positioning a needle hub in said slot.

4. A closure assembly according to claim 1 wherein:
   said closure has a circular disc configuration defined by a peripheral edge;
   a circular flange extending radially outward beyond said peripheral edge on one side of said disc; and
   a plurality of tabs extending beyond said peripheral edge on the other side of said disc, said flange and said tabs for engaging opposite sides of said annular portion for rotatably mounting said disc in said central opening in said container.

5. A closure assembly according to claim 1 wherein said means constraining said closure to rotate in a single direction of rotation comprises ratchet means acting between said circular closure and said circular frame.

6. A closure assembly according to claim 5 wherein said ratchet means comprises a tab on an inside of said closure and a plurality of ratchet teeth on said circular rim.

7. A closure assembly according to claim 6 wherein said needle removal slot means comprises an elongated converging slot converging in said direction of rotation, and having an enlarged end with an overlying semicircular lip for overlying a needle hub for applying a force thereto.

8. A closure assembly according to claim 7 wherein said slot is partially surrounded by a vertically spaced rim for engaging an end of a syringe barrel for positioning a hub of a needle in said slot.

9. A closure assembly according to claim 8 wherein said means constraining said closure to rotate in a single direction of rotation comprises ratchet teeth on said circular frame, and a tab on an inside of said closure for engagement with said ratchet teeth.

10. A rotatable needle removal closure assembly comprising in combination:
    a container having a circular edge portion defining a circular central opening;
    a disc rotatably mounted on said edge portion within said central opening;
    means confining said disc to a single direction of rotation; and
    needle coupling means on said disc offset from the rotary axis thereof for coupling a needle thereto for rotation of said needle therewith for unthreading said needle from a holder upon said rotation of said disc in said direction of rotation.

11. A closure assembly according to claim 10 wherein:
    said rotatable disc is defined by a peripheral edge;
    a circular flange extending radially outward beyond said peripheral edge on one side of said disc; and
    a plurality of tabs extending beyond said peripheral edge on the other side of said disc, said flange and said tabs for engaging opposite sides of said annular portion for rotatably mounting said disc in said central opening in said container.

12. A closure assembly according to claim 11 wherein said means constraining said closure to rotate in a single direction of rotation comprises ratchet teeth on said circular frame, and a tab on an inside of said closure for engagement with said ratchet teeth.

13. A closure assembly according to claim 11 wherein said needle removal slot means comprises an elongated converging slot converging in said direction of rotation, and having an enlarged end with an overlying semicircular lip for overlying a needle hub for applying a force thereto.

14. A closure assembly according to claim 13 wherein said slot is partially surrounded by a vertically spaced rim for engaging an end of a syringe barrel for positioning a hub of a needle in said slot.

15. A closure assembly according to claim 10 wherein said needle removal slot means comprises an elongated converging slot converging in said direction of rotation, and having an enlarged end with an overlying semicircular lip for overlying a needle hub for applying a force thereto.

16. A closure assembly according to claim 15 wherein said slot is partially surrounded by a vertically spaced rim for engaging an end of a syringe barrel for positioning a hub of a needle in said slot.

17. A closure assembly having a needle removal slot, comprising in combination:
    a container having a circular edge portion defining a circular open end;
    a closure including an annular portion having a central opening fixed on said container upper edge portion; and
    a needle removal slot in said closure offset from a central axis thereof for receiving and engaging a needle hub for threadably removing said needle from a holder upon rotation of said holder, said slot means comprises an elongated converging slot converging from an enlarged end to a narrow end, said enlarged end having an overlying semicircular lip for overlying a needle hub for applying a force thereto, said slot is partially surrounded by a vertically spaced rim for engaging an end of a syringe barrel for positioning a hub of a needle in said slot.

18. A closure assembly according to claim 17 wherein:
    said closure includes a disc rotatably mounted on said edge portion within said central opening;
    means confining said disc to a single direction of rotation;

said rotatable disc is defined by a peripheral edge;
a circular flange extending radially outward beyond said peripheral edge on one side of said disc; and
a plurality of tabs extending beyond said peripheral edge on the other side of said disc, said flange and said tabs for engaging opposite sides of said annular portion for rotatably mounting said disc in said central opening in said container.

19. A closure assembly according to claim 18 wherein said means constraining said closure to rotate in a single direction of rotation comprises ratchet teeth on said circular edge portion, and a tab on an inside of said closure for engagement with said ratchet teeth.

20. A closure assembly according to claim 18 wherein said needle removal slot means comprises an elongated converging slot converging in said direction of rotation, and having an enlarged end with an overlying semicircular lip for overlying a needle hub for applying a force thereto.

* * * * *